United States Patent [19]

Song

[11] Patent Number: 4,670,398
[45] Date of Patent: Jun. 2, 1987

[54] PLANT TISSUE CULTURE VESSEL AND FILTER

[76] Inventor: John S. Song, 2827 Sheridan Pl., Evanston, Ill. 60201

[21] Appl. No.: 832,858

[22] Filed: Feb. 24, 1986

[51] Int. Cl.$^4$ ............................................. C12M 1/22
[52] U.S. Cl. .................................. 435/298; 220/366; 47/66
[58] Field of Search ............... 435/284, 287, 297, 298, 435/299, 311, 810, 300, 301; 220/360, 361, 366, 371, 355; 47/1.1, 66, 69, 84

[56] References Cited

U.S. PATENT DOCUMENTS

| | | | |
|---|---|---|---|
| 1,513,360 | 10/1924 | Ablahadian | 435/296 |
| 3,297,184 | 1/1967 | Andelin | 435/296 |
| 4,014,501 | 3/1977 | Buckenmayer | 220/366 |
| 4,244,765 | 9/1980 | Song . | |
| 4,291,493 | 9/1981 | Monson | 47/84 |
| 4,299,921 | 11/1981 | Youssef | 435/298 |
| 4,358,908 | 11/1982 | Song . | |

Primary Examiner—Samuel Scott
Assistant Examiner—Noah Kamen
Attorney, Agent, or Firm—Lloyd L. Zickert

[57] ABSTRACT

A plant tissue culture vessel including a base and a mating cover wherein the base and cover include means for adjustably setting the gas exchange rate between the interior of the vessel and the ambient, and means for selectively defining a loose or tight fit between the cover and the base. The cover and base are made from a material that permits the transmission of light. A filter is provided between the mating parts of the cover and base to filter contaminants during all modes of relationship between the cover and the base. The filter is constructed from a foam urethane blank having a porosity capable of precluding the passage of dust, bacteria and virus and is formed as an endless member by being cut in strip form from a blank of material and thereafter longitudinally slit between the ends.

15 Claims, 16 Drawing Figures

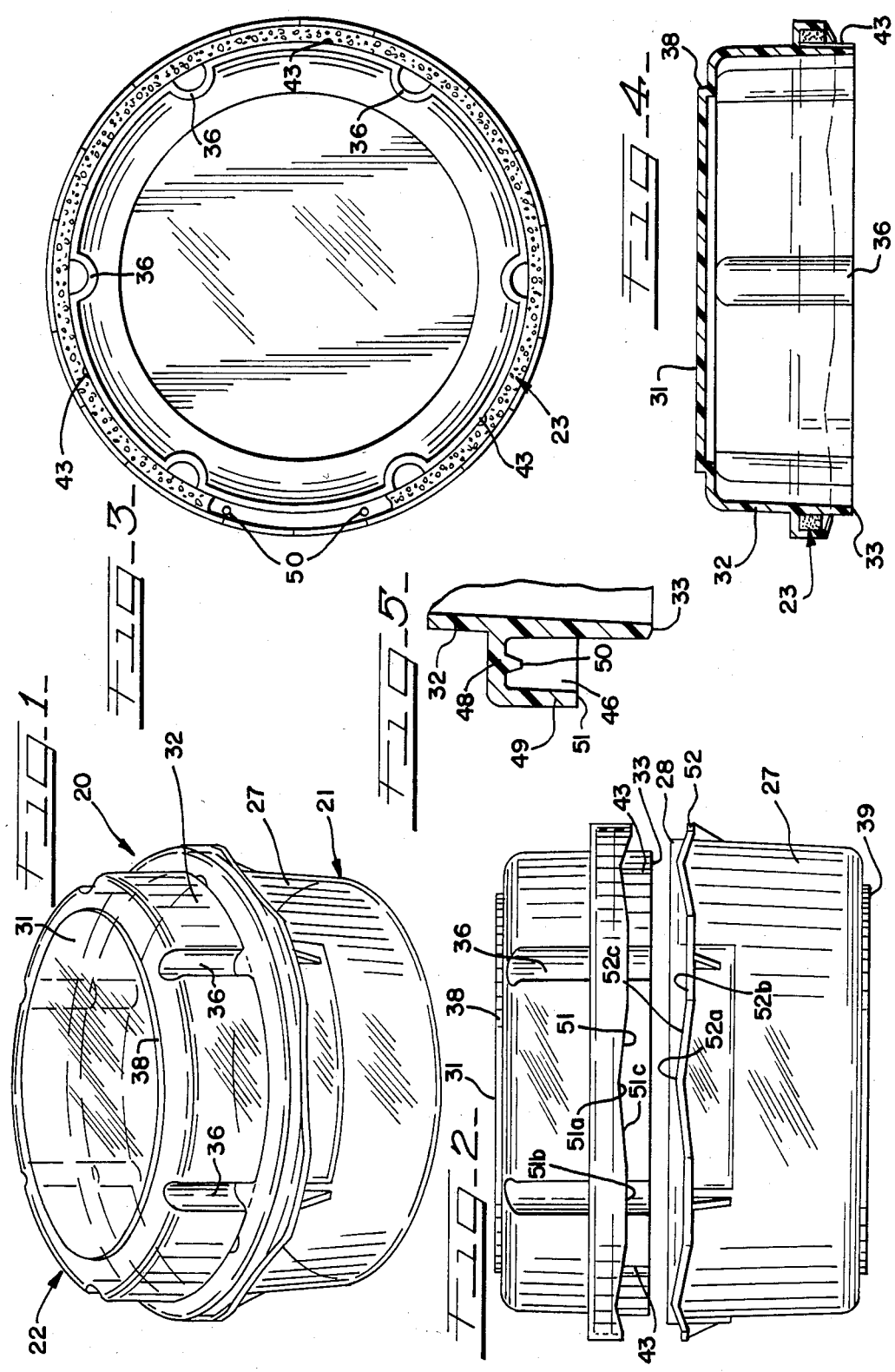

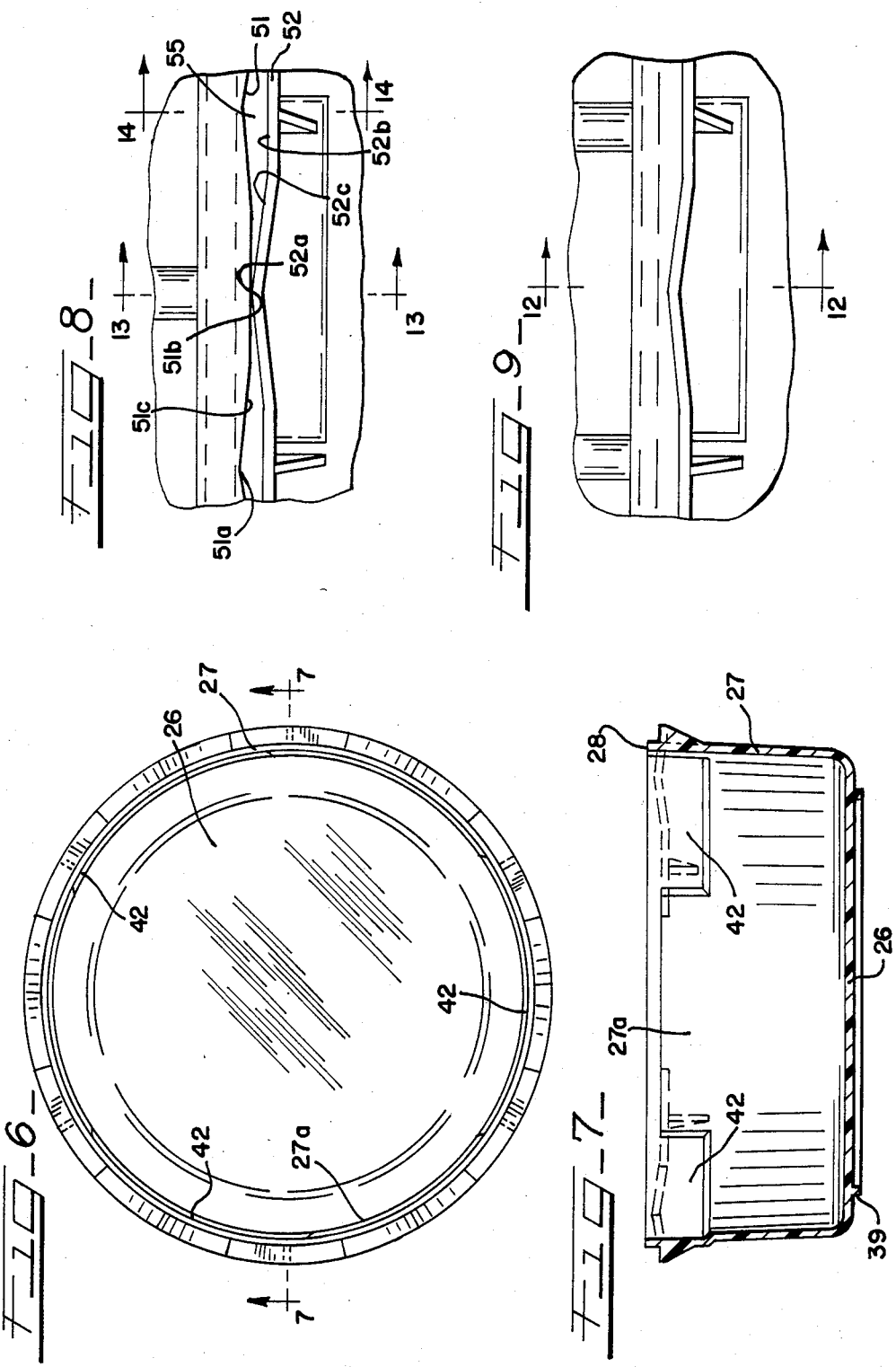

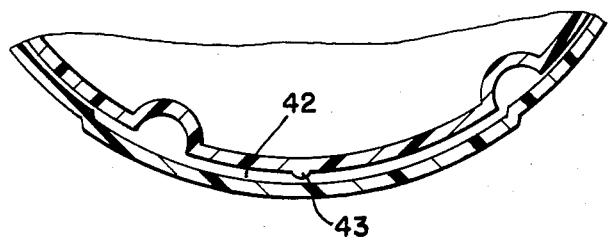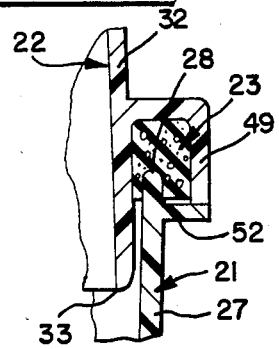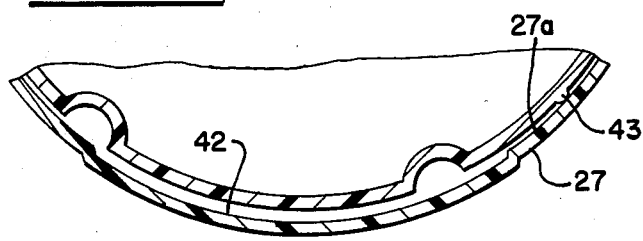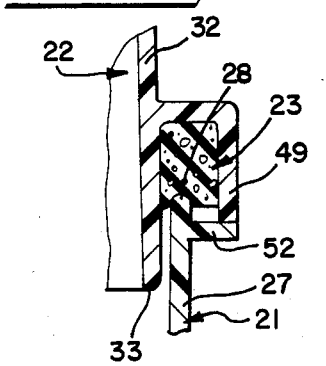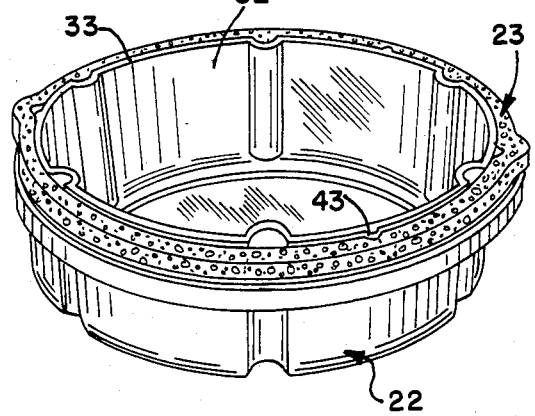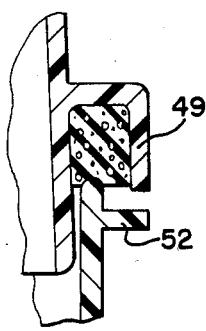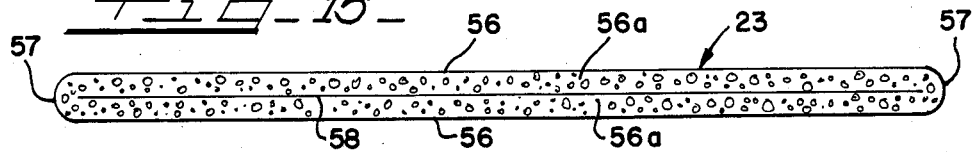

PLANT TISSUE CULTURE VESSEL AND FILTER

DESCRIPTION

This invention relates in general to a plant tissue culture vessel for use in growing plant tissue cultures in laboratory environments, and more particularly to a vessel that permits the varying of the gas exchange rate between the interior of the vessel and the ambient, and still more particularly to a vessel having a gas exchange filter that is endless and formed from a blank of filter material for eliminating contamination during gas exchange.

BACKGROUND OF THE INVENTION

Heretofore, plant tissue culture vessels or containers have been known and capable of providing various growth conditions as in the vessel disclosed in U.S. Pat. No. 4,358,908. However, this vessel may not be operated to easily adjust the gas exchange rate between the interior and the ambient, and it is not economical to use non-autoclavable filters for such a vessel. Some plant tissue culture containers do not have filters and filters used in others are not fine enough to filter out dust, bacteria or virus. It has been known to minimize contamination by growing plant tissue cultures in clean chambers that have filtered air. Such clean chambers are expensive to construct, operate and maintain. Even so, because of personnel and material traffic through clean chambers, some contamination through gas exchange cannot be avoided. Since known plant tissue culture containers or vessels are not in themselves contamination-proof, the plant tissue cultures are not free from contamination even in clean room environments.

Because known culture containers are not contamination-free, they must be sealed with tape during shipping. The tape seals are often damaged and the media within the container is disturbed when the containers are suddenly subjected to lower air pressure as during air shipping. Such containers do not allow equalizing air pressure with contamination-free air exchange. Those containers with tight tape seals do not allow sufficient gas exchange, thereby preventing proper plant growth.

Currently used containers have generally fixed spacing between cover and base for gas exchange. Such fixed spacing is excessive for some cultures particularly when the cultures are grown over long periods of time and insufficient for others. Other containers are too tight and therefore do not allow sufficient gas exchange, thereby retaining ethylene or moisture to prevent proper plant growth. Present containers cannot readily adjust the gas exchange rate.

Covers of known containers or vessels are tightly mounted on or screwed onto the base, thereby requiring both hands of a laboratory technician to close or remove the cover. The cover for the container of the above patent fits tightly on the base. This leads to inefficiency in container handling and higher costs, particularly during transplanting at the hood. Some current covers have totally loose covers which are not safe when the units are moved around during handling, and it is preferable to have tightly held covers during shipping and even during incubation. No known culture container allows for the adjustment of the tightness of the cover on the base.

When culturing different plants, containers of different heights are needed. For operations at the hood, planting or transplanting, when the body or base of the container is lower, it is easier to reach and more efficient. For most plants, the bases have to be tall enough to prevent the leaves from falling over the edges to allow the covers to be reclosed. Containers with short bases and tall covers are preferred for plants that grow straight up. Current reusable containers cannot be used upside-down in order to change the relative heights of the covers and bases because they include a drip ring, usable only in the upright position, to prevent condensation forming after autoclaving from leaking into the opening between the cover and base and causing contamination.

Heretofore, most plastic covers for plant tissue culture vessels are made of polypropylene for flexibility and autoclavability features. Polypropylene is objectionable in that it is translucent and does not allow total light transmission, thereby losing some light energy.

Satisfactory filters heretofore used have been expensive and difficult to manufacture. Further, known filters or filtering tapes are not fine enough to filter dust, bacteria or virus. Some permeable tapes do not allow enough gas exchange.

SUMMARY OF THE INVENTION

The present invention overcomes the difficulties heretofore known in plant tissue culture vessels and provides a contamination-proof vessel having the capability of adjusting the gas exchange rate and the tightness between the cover and the base.

The plant tissue culture vessel of the present invention is cylindrically shaped and includes a base, a cover and a filter held by the cover. It is made of a suitable clear relatively rigid plastic material, such as polystyrene, so that it provides the maximum light transmission to the contents. Means is provided on the cover and base to permit selective loose or tight fit relationship between the cover and base. The mating portions of the cover and base define an adjustable feature for varying the gas exchange rate between the interior of the vessel and the ambient. A filter is retained in the cover to coact with the cover and the base for filtering the gas flow between the interior and the ambient at all adjusted positions of the cover and base. This filter is made from a reticulated, fully "open-pore", flexible, ester type of polyurethane foam or equivalent material having a fine totally open cell structure to provide a filter of about 100 pores per inch (PPI) whereby dust, bacteria and virus are filtered while allowing ample gas flow. Preferably, the filter will be of 100 PPI or finer. Moreover, the filter is sterilizable with gas or radiation. Since it is not practical for culture laboratories to use gas or radiation sterilization for reuse of the vessel, the vessel of the present invention is disposable. Accordingly, there is no need to provide for vessel autoclaving, washing, drying or extra storage. Further, when the filter is properly in place, and the vessel is not tampered with or damaged, there will be no contamination due to gas exchange.

Because the cover and base are formed to selectively provide loose or tight fitting conditions, when adjusted for loose fit the cover may be picked up with one hand while not disturbing the bottom or base. This is particularly advantageous at the hood for planting. When it is desired to carry the entire vessel by the top or cover, or otherwise condition the vessel for shipping, the cover is rotated to place it in tight-fitting relation with the bottom or base so that the top and bottom can be held together.

Mating undulating edges of the cover and base permit varying the gas exchange rate by relative rotation between the cover and base. By turning the top relative to the bottom, the spacing between the top and bottom will increase or decrease for maximum or minimum gas or moisture exchange and remain at any set position.

The vessel of the present invention is also constructed so that it may be used in upright or upside-down position. The top of the cover and the bottom of the base are also provided with coacting elements so that the containers may be stacked and locked against relative lateral movement therebetween.

It is therefore an object of the present invention to provide a new and improved plant tissue culture vessel or container.

A further object of the invention is to provide a plant tissue culture vessel that need not be used in a clean chamber.

Another object of the invention is in the provision of a new and improved plant tissue culture vessel having a cover and base that when assembled is contamination-proof, adjustable to vary the gas exchange rate between the interior and the ambient, and selectively capable of having the cover loosely or tightly fit on the base.

A further object of the present invention is to provide a plant tissue culture vessel made from a light-transmitting plastic material and which is disposable, thereby eliminating the need to provide vessel autoclaving, washing, drying or extra storage.

A still further object of the present invention is to provide a plant tissue culture vessel having a cover and base wherein the cover may be selectively tightly or loosely fit on the base to facilitate handling.

A further object of the present invention is to provide an inexpensive and efficient filter for a plant tissue culture vessel capable of filtering dust, bacteria and virus.

A further object of the present invention is to provide a contamination-proof plant tissue culture vessel capable of adjusting the air pressure in the vessel as during air transportation without disturbing the media or causing contamination.

Another object of the present invention is in the method of economically making and installing a filter for a plant tissue culture vessel.

Other objects, features and advantages of the invention will be apparent from the following detailed disclosure, taken in conjunction with the accompanying sheets of drawings, wherein like reference numerals refer to like parts, in which:

DESCRIPTION OF THE DRAWINGS

FIG. 1 is a perspective view of the plant tissue culture vessel of the present invention with the cover in place on the base;

FIG. 2 is an exploded elevational view of the vessel of the present invention but illustrating the filter in position on the cover;

FIG. 3 is a bottom plan view of the cover;

FIG. 4 is a transverse sectional view taken through the cover;

FIG. 5 is a greatly enlarged fragmentary detailed sectional view taken through the cover outer wall with the filter removed from the filter cavity;

FIG. 6 is a top plan view of the bottom or base of the vessel of the present invention;

FIG. 7 is a transverse sectional view taken through the base and substantially along line 7—7 of FIG. 6;

FIGS. 8 and 9 are fragmentary and greatly enlarged detailed side elevational views of the container illustrating the gas exchange rate adjusting feature of the vessel and wherein the cover is adjusted relative to the base in FIG. 8 to provide the maximum rate of gas exchange and in FIG. 9 for the minimum gas exchange rate;

FIGS. 10 and 11 are fragmentary cross-sectional views taken through the cover and base in assembled relation to illustrate the means for providing selective loose and tight fitting relation between the cover and base;

FIGS. 12 and 13 are greatly enlarged fragmentary vertical sectional views taken through the cover and base side walls to illustrate the relationship between the cover and base in the maximum and minimum gas exchange rate positions, and are respectively taken generally along lines 12—12 of FIG. 9 and 13—13 of FIG. 8;

FIG. 14 is a sectional view like FIGS. 12 and 13 but taken along line 14—14 of FIG. 8 where the gap is defined between the cover and base;

FIG. 15 is a plan view of a filter prior to its installation on a cover member; and FIG. 16 is a bottom perspective view of a cover member and illustrating the first step of installing a filter on the cover.

DESCRIPTION OF THE INVENTION

Referring now to the drawings, and particularly to FIGS. 1 to 7, the plant tissue culture vessel or container of the present invention is generally designated by the numeral 20 and includes a base member or bottom 21, a cover member or top 22, and a filter 23 which is mounted in the cover. Both base and cover members are generally cup-shaped. As seen in FIG. 1, the cover and base are in assembled relation, while in FIG. 2 the cover is raised from the base. Further, the filter 23 is shown in FIG. 14 before it is mounted in place on the cover.

The cover and base are molded from a clear or transparent polystyrene material, or the equivalent, which is relatively rigid, although some flexibility is provided in the side walls and utilized when the cover is in tight-fitting relation with the base as will be hereinafter described. It is important to have the plastic material transparent in order to provide the best possible light transmission for growing plant tissue cultures. It is also preferable that both the cover and the base be transparent essentially to the extent that they are optically clear. However, if there is a need to utilize the container of the invention where the presence of light for growing purposes would not be desired, it may be appreciated that the plastic material of the container could be translucent or of any desired opacity and further that the opacity of the cover may be different from that of the base.

The coacting parts of the cover and base function to selectively produce loose or tight fitting relation between the cover and base and variable spacing between the members when they are in assembled relation so that a variable gas exchange rate can be obtained by adjusting the relative rotational positions between the cover and base. Further, the coacting parts allow the mounting of a filter on one of the parts so that the gas exchange between the interior of the container and the ambient is filtered against contaminants, thereby preventing the contamination of the environment within the container.

The base 21 includes a generally flat bottom or end wall 26 and an upstanding substantially vertical or side wall 27. There is a slight taper in the wall to facilitate molding. The upstanding wall 27 terminates in an upper edge 28 that is in a horizontal plane whereby the height of the wall is uniform throughout its circumferential extent. The cover includes a generally flat top or end wall 31 and a downwardly extending cylindrical side wall 32 terminating in a lower edge 33 that also is in a common horizontal plane. Thus, the height of the side wall 32 is uniform throughout its circumferential extent. The cover side wall 32 includes a plurality of vertically extending and inwardly projecting ribs 36 which, while having no special function than to facilitate the molding of the cover, do somewhat serve to reinforce the cover side wall. These ribs are circumferentially equally spaced apart, as particularly seen in FIG. 3.

The top wall 31 of the cover includes a central portion that is slightly raised, thereby defining a shallow nesting wall 38 which coacts with a shallow nesting lip or ledge 39 projecting downwardly from the bottom wall 26 of the base 27. The outer diameter of the nesting wall 38 is slightly smaller than the inner diameter of the nesting lip 39 so that when one vessel is stacked on another, the nesting or stacking wall 38 will be telescopically received within the nesting or stacking lip 39 to lock stacked vessels against relative lateral movement. Thus, the uppermost stacked vessel cannot slide off the next lower vessel.

It may be appreciated that the stacking elements may be reversed in position where the lip would project upwardly from the cover and the stacking wall project downwardly from the base. Further, it is appreciated that the cover may function as the base or bottom of the container and the base or bottom may function as the cover or top of the container. Thus, the container may be used upside down, and where the cover and base height are unequal, the height of the cover would change. While the depth of the cover is less than that of the base in the illustrated embodiment, they may be equal or otherwise dimensioned depending upon the type of plant tissue culture to be grown.

The outer diameter of the cover side wall 32 is slightly less than the inner diameter of the base side wall 27 so that the side wall of the cover may be telescopically received within the side wall of the base. Further, the dimensions are such that the fit is somewhat loose so that there is no binding between the walls.

In order to define both loose and tight fitting relationships between the cover and the base along the upper edge 28 of the base at circumferentially equally spaced apart positions, arcuate recesses 42 are formed. As seen most clearly in FIGS. 6, 7, 10 and 11, these recesses coact with outwardly projecting and vertically extending ribs 43 when the cover is assembled with the base such that the ribs mate with the recesses 42. The ribs 43 are likewise circumferentially equally spaced apart and of the same number as the recesses. It may be appreciated that while the cover is assembled to the base, rotation of the cover relative to the base to the amount that the ribs 43 remain in mating relation with the arcuate length of the recesses 42 continues to maintain the loose fit between the cover and the base. Thus, the cover may be rotated a limited amount depending upon the arcuate length of the recesses and still maintain the loose fit with the base, as a radius extending to the outer surface of the ribs is shorter than a radius extending to the inner surface of the recesses. Further, the radius of the ribs 43 slightly greater than the radius extending to the inner surface 27a of the wall 27 such that when the ribs are aligned with the wall surface 27a and therefore at a position between the ends of adjacent recesses, an interference fit is defined between the cover and the base producing a tight-fitting relation.

In the loose-fitting relation the cover may easily be lifted by one hand from the base without disturbing the base and without the need to restrain the base. In the tight-fitting position the entire container may be lifted by merely applying a lifting force to the cover, as the frictional engagement between the ribs 43 and the side wall 27 is such as to overcome the weight of the base and any contents. Thus, in the tight-fitting relation, the containers may easily be moved from one position to another position without separating the cover from the base or disturbing the gas exchange rate and filtering operation. Further the containers can be shipped and still maintain the assembled relation without disturbing the contents. As will be more fully explained hereafter, gas exchange rate between the interior and the ambient may be gradually varied between minimum and maximum while the cover is in either loose-fitting or tight-fitting relation.

The cover 22 includes a downwardly opening annular filter receiving channel 46 for receiving the filter 23 that serves to filter contaminants. The channel 46 is defined by a radially outwardly projecting wall 48 and from its free edge a downwardly projecting skirt wall 49. The filter channel also serves to receive the upper end of the base wall when the cover is mounted on the base. A plurality of circumferentially spaced apart tits 50 project from the radial wall 48 into the filter channel or cavity 46 for engagement by the filter 23 to inhibit rotational movement of the filter during relative rotational movement between the cover and the base.

The free edge 51 of the skirt wall 49 is undulated to define cam surfaces for coacting with a radially outwardly extending and oppositely formed undulating ledge 52 of the base 21. Thus, the undulating cover edge 51 coacts with the undulating base ledge 52 when the cover is assembled to the base, as shown in FIG. 1, and for the purpose of varying the spacing between the base and the cover when rotating one relative to the other, as illustrated in FIGS. 8 and 9. Accordingly, the cover edge 51 and the base ledge 52 are respectively provided with mating upwardly and downwardly inclined portions and low points and high points so that the spacing between the cover and base may be infinitely varied between a maximum and minimum position by relative rotation between the cover and base, particularly as seen in FIGS. 1, 2, 8 and 9. The undulating cover edge includes low points 51a, high points 51b and sloping surfaces 51c therebetween, while the base undulating ledge 52 includes high points 52a, low points 52b, and sloping surfaces 52c therebetween. When the cover is rotated relative to the base such that a high point 52a of the base aligns with a low point 51a of the cover, likewise the low parts 52b align with the high parts 51b, as seen in FIG. 9, and this represents the minimum gas exchange rate position of the cover and base. It will be appreciated that without a seal member between the edge 51 and the ledge 52, there will always be a gas exchange passage therebetween. Further, when the high point 52a aligns with a high point 51b of the cover, as seen in FIG. 8, the cover will be spaced a maximum distance apart from the base providing a plurality of large gas exchange openings 55 in circumferentially spaced relation to define the maximum gas exchange rate available for the vessel.

It will be further appreciated that at all positions between that shown in FIG. 8 and that shown in FIG. 9 the cover will be spaced from the base to produce a gas exchange rate between the maximum and minimum. Therefore, rotation of the cover relative to the base adjusts the gas exchange rate for the container because the cover can be selectively mounted on the base for either loose-fitting arrangement or tight-fitting arrangement as previously described. The number of sets of opposed mating high and low parts of the undulating cover edge and undulating base ledge are twice in number to the number of arcuate recesses 42 on the base and interfering ribs 43 on the cover. Therefore, the adjustment of the gas exchange rate between minimum and maximum can be made when the cover and base are in the loose-fitting mode and in the tight-fitting mode. The relationship of the interfering ribs and the high and low parts of the undulating cover edge as well as the relationship between the high and low parts of the base ledge to the recesses 42 is such as to accomplish the foregoing function.

The filter 23 is made from an intercellular polyurethane foam material or equivalent having at least 100 pores per inch (PPI) so that it will filter dust, bacteria and virus. As previously noted, the filter material is a reticulated, fully "open-pore", flexible, ester type of polyurethane foam, such as Scott Industrial Foam made by Scott paper Company of Chester, Pa. Additionally, the material is compressible and resilient, and gas or radiation sterilizable. The filter is mounted in the cover and in the gas exchange passage when the cover is mounted on the base such as to filter the gas exchange in all modes of operation of the cover with respect to the base. Thus, the filter operates to provide a contamination-proof environment within the vessel during the growing of plant tissue cultures. The filter will function to completely cover the gas exchange passage when the cover is positioned to provide either minimum or maximum gas exchange rate. In this regard the filter cross section is such that it fully and tightly engages all surfaces in the filter-receiving channel 46 as well as the base upper edge 28, as illustrated in FIGS. 12 to 14. The dimensions of the filter are such that it will be slightly compressed width-wise when mounted in the filter-receiving channel to tightly engage the channel-receiving surfaces and slightly compressed depth-wise by the base side wall, as seen in FIGS. 12 to 14. Thus, the base side wall upper edge 28 projects slightly into the filter compressing the area of engagement even at minimum penetration, and assuring at all times complete coverage of the gas exchange passage defined between the upper edge of the base side wall and the surfaces of the filter-receiving channel and the side wall 32 of the cover. Accordingly, the vessel is contamination-proof.

The filter 23 is uniquely made by die-cutting it from a blank of filter material. A sheet of material is selected having the desired thickness of the flter relative to its vertical height as viewed in mounted relation in the cover and then cut in the shape illustrated in FIG. 15 which defines an elongated strip having rounded ends. The top plan view in FIG. 15 shows that the cut filter includes opposed straight sides 56 and opposed curved ends 57. Additionally, this form is slit through the middle at 58. The slit is equally spaced between the opposite sides 56 and terminates short of the ends 57 at a distance substantially equal to the distance between the slit 58 and one of the sides 56 so that the thickness of the filter as horizontally viewed in its mounted position on the cover will be substantially the same throughout its circumferential body. Thereafter, separating the sides 56a results in producing a seamless, endless filter that can be mounted in the annular filter-receiving channel 46 and function to fully filter the gas exchange passage between the cover and the base.

The first step in mounting the filter in place is illustrated in FIG. 16 where the filter form of FIG. 15 is opened and disposed over the side wall 32 of the cover. Thereafter, it is gently pushed into the filter-receiving channel until it bottoms and is fully mounted. As previously expressed because the horizontal width of the filter when made is slightly greater than the horizontal dimension of the filter-receiving channel, it is necessary that the sides of the filter be compressed slightly together when positioning the filter within the channel. It then can be appreciated that the filter will be frictionally held within the channel and not fall out when the cover is lifted, and will completely fill the cavity such that air going into the vessel will be filtered. As previously mentioned, the filter would also be bottomed and engaged by the plurality of tits 50 to prevent relative rotational movement between the filter and the cover when a rotational force is applied by engagement with the base as the cover is rotated relative to the base. Thus, the integrity of the filter is maintained during all modes of operation of the container and is not disturbed when the cover is rotated relative to the base to vary the gas exchange rate.

In operation a base would be taken and implanted with a plant tissue culture. A cover of suitable size would then be mounted on the base in either a loose-fitting mode where the interfering ribs 43 would align with the recesses 42, as shown in FIG. 10, or in the tight-fitting mode where the interfering ribs 43 would be disposed between the recesses 42, as illustrated in FIG. 11. Once the cover is brought to its fully seated position, it would then be rotationally disposed relative to the base to define the desired spacing between the cover and base and therefore the desired gas exchange rate. The filter is fully operational when the cover is seated and rotated to any position, as illustrated in FIGS. 12 to 14. The gas exchange flow, if going out of the container, will go between the cover and base walls upwardly through and over the edge 28 of the base wall and downwardly along the inside of the skirt wall 49 and outwardly between the undulating edge 51 of the skirt wall and the undulating ledge 52 to the ambient, and, if going into the container, the opposite. The vessel would then be contamination-proof in any mode of operation, and subsequent adjustments between the cover and base may be made as would be desired for further growing conditions and use of the vessel. Because the cover can be in tight-fitting relation with the base, there is no need to tape the cover onto the base for shipping, thereby preserving the desired gas exchange rate at all times.

It will be understood that modifications and variations may be effected without departing from the scope of the novel concepts of the present invention, but it is understood that this application is to be limited only by the scope of the appended claims.

I claim:

1. A plant tissue culture vessel comprising a base member, a cover member, and a filter of resilient and compressible material, said members each being generally cup-shaped and including a substantially flat end wall and a substantially cylindrical side wall extending from the end wall, said cylindrical walls sized so that one of said walls will be freely telescopically received within the other of said walls when the members are assembled, the member having its cylindrical wall telescopically received within the cylindrical wall of the other member having an outer cylindrical skirt wall concentric therewith for overlying in part the outer surface of the cylindrical wall of said other member and defining a filter cavity, the cylindrical wall of said other member having an intergral annular edge extending into the filter cavity and an annular undulating outwardly projecting stop ledge spaced downwardly from said edge, said skirt wall having an undulating edge facing and coacting with said stop ledge to define an adjusting device for varying the spacing between the members at varying rotational positions therebetween to vary rate of gas exchange between the vessel interior and the ambient, the relationship between the members at any rotational position defining therebetween a gas exchange passage between peripheries of said members to permit gas exchange between the interior of the vessel and the ambient, and said filter being disposed in said filter cavity in said gas exchange passage to filter the gas exchange at any relative rotational position between the base and cover.

2. The vessel of claim 1, which further includes means on one member coacting with means on the other member for selectively defining a loose or tight fit therebetween depending on the relative rotational positions of said members.

3. The vessel of claim 1, which further includes means on the end walls of said members defining interfitting vertical stacking means.

4. A vessel as defined in claim 1, wherein said base and cover members are molded of light-transmitting polystyrene.

5. A vessel as defined in claim 1, wherein said filter is of a material capable of filtering dust, bacteria and virus while allowing ample gas exchange.

6. A vessel as defined in claim 5, wherein said filter is of intercellular material.

7. A vessel as defined in claim 6, wherein said filter material is about 100 PPI.

8. A vessel as defined in claim 7, wherein said material is foam polyurethane.

9. A plant tissue culture vessel comprising a base, a cover, and a filter, said base and cover being generally cup-shaped, said base having a bottom wall and an upstanding generally cylindrical side wall, said cover having a top wall and a downwardly extending generally cylindrical side wall, said cylindrical side walls sized so that the cover side wall is freely telescopically receivable within the base side wall when the cover and base are assembled, said cover having an outer cylindrical skirt concentric with the side wall and defining a filter cavity and disposed to overlie in part the side wall of the base, whereby the upper edge of the base side wall extends into the filter cavity, said base further including a radially outwardly extending stop ledge having an upwardly facing undulated surface, the downwardly facing edge of said skirt being undulated and coacting with the undulated surface of said stop ledge to define an adjusting device for varying the vertical relationship between said cover and base upon relative rotational movement between the base and cover to thereby vary the gas exchange rate between the interior of the vessel and the ambient, and said filter being disposed in said filter cavity and engageable by the cover and base to filter the gas flow between the interior of the vessel and the ambient.

10. A vessel as defined in claim 9, wherein said base and cover further include coacting means for selectively defining loose or tight fitting relation between said base and cover.

11. A vessel as defined in claim 10, wherein said coacting means includes a plurality of equally spaced apart arcuate recesses on the interior surface of said base side wall, and an equal number of equally spaced apart outwardly projecting elements on the cover sized to tightly fit the interior surface of said base side wall and loosely fit in the recesses to selectively define a tight or loose fitting relationship between the cover and base.

12. A vessel as defined in claim 11, wherein the base and cover are molded of a clear, light-transmitting, generally rigid plastic.

13. A vessel as defined in claim 12, wherein the filter is of a resilient and compressible intercellular material of about 100 PPI.

14. A vessel as defined in claim 13, wherein the filter is sized to be compressibly received in the filter cavity and compressibly engaged by the base side wall.

15. A vessel as defined in claim 14, wherein the intercellular material is a foam polyurethane.

* * * * *